United States Patent [19]

Shawl et al.

[11] Patent Number: 4,883,908
[45] Date of Patent: Nov. 28, 1989

[54] PROCESS FOR THE PREPARATION OF AROMATIC ISOCYANATES FROM DIALKYL UREAS USING AN ORGANIC SULFONIC ACID PROMOTER

[75] Inventors: Edward T. Shawl, Wallingford; Haven S. Kesling, Jr., Drexel Hill; Frank J. Liotta, Jr., Collegeville, all of Pa.

[73] Assignee: Arco Chemical Technology, Inc., Wilmington, Del.

[21] Appl. No.: 305,356

[22] Filed: Feb. 2, 1989

[51] Int. Cl.$^4$ ............................................. C07C 69/00
[52] U.S. Cl. .................................................... 560/344
[58] Field of Search ........................................ 560/344

[56] References Cited

U.S. PATENT DOCUMENTS

| | | | |
|---|---|---|---|
| 3,898,259 | 8/1975 | Hearsey | 560/344 |
| 3,936,484 | 2/1976 | Rosenthal et al. | 560/344 |
| 4,153,624 | 5/1979 | Fern et al. | 560/344 |
| 4,223,145 | 9/1980 | Hentschel et al. | 560/344 |
| 4,596,679 | 6/1986 | Hellbach et al. | 560/344 |

*Primary Examiner*—Alan Siegel
*Attorney, Agent, or Firm*—Delbert E. McCaslin

[57] ABSTRACT

An improved process is provided for the preparation of aromatic mono- and poly-isocyanates by the thermal decomposition of an aromatic bis dialkyl urea in solvent in the presence of an organic sulfonic acid or sulfonated aromatic ion exchange resin as a promoter for conversion of the urea groups to isocyanates.

16 Claims, No Drawings

PROCESS FOR THE PREPARATION OF AROMATIC ISOCYANATES FROM DIALKYL UREAS USING AN ORGANIC SULFONIC ACID PROMOTER

FIELD OF THE INVENTION

The present invention relates to an improved process for the preparation of aromatic mono- and polyisocyanates by heating in an inert solvent an aromatic bis dialkyl urea in the presence of an organic sulfonic acid such as methane sulfonic acid as a promoter to convert the urea groups to isocyanate groups and recovering the aromatic isocyanate from the reaction mixture.

BACKGROUND OF THE INVENTION

A number of processes have have been reported for the preparation of aromatic mono- and polyisocyanates by the vapor or solvent phase decomposition of substituted ureas.

The vapor phase production of aromatic isocyanates from symmetrical bis aryl ureas in the presence of hydrogen chloride,phosphorus pentoxide or zinc chloride was described by A. Hofmann in the Proc. Royal Soc., London, Vol. IX, p. 274 (1858). By heating a mixture of diphenyl urea with phosphorus pentoxide, zinc chloride or gaseous HCl. Hofmann distilled phenyl isocyanate ovehead. No details of the experimental procedure are presented and yield of isocyanate not given.

A. Hofmann, Chemisch Berichte, Vol. 3, pp. 653–658 (1870) described heating diphenyl urea in the presence of phosphoric acid giving yields too small to be considered for the preparation of the isocyanate.

Subsequent work by Iwakura and Nagakubo reported in the Bulletin Tokyo Inst. Technol., Vol. 13, p.25 (1950) and Chemical Abstracts, Vol.44, p. 3924e (1950) describes the preparation of an aromatic isocyanate (p-ethoxyphenylisocyanate) by heating a solution of bis aryl urea such as bis (p-ethoxyphenyl) urea in the presence of hydrogen chloride gas.

The vapor phase decomposition of bis aryl ureas at 350° C. and higher temperatures has been described by W.D. Bennet et al, Journ. Am. Chem. Soc., Vol. 75, p.2101 (1952) and Slocombe et al in U.S. Pat. No. 2,773,086, Dec. 4, 1956 in the presence of gaseous HCl as a promoter. Yields are reported in the 60 to 70% range for the vapor phase reaction and only a 5% yield for liquid phase reaction. A carbamoyl chloride intermediate is formed.

The liquid phase decomposition of trisubstituted ureas to isocyanates has been described by van Landeghem et al, French Pat. No. 1,473,821, Feb. 13, 1967; C. J. Hearsey, U.S. Pat. No. 3,898,259, Aug. 5, 1975 and Rosenthal et al in the U.S. Pat. No. 3,936,484, Feb. 3, 1976. van Landeghem shows thermal decomposition of trisubstituted ureas in an organic solvent having specified dielectric constants at 140° to 170° C. with long reaction times of from 6 to 10 hours and modest yields of 60 to 75%. A variety of catalysts are shown but not exemplified or claimed, and include metal salts, such as acetates, stearates, and linoleates of manganese, zinc, cobalt, chromium and vanadium, tertiary amine bases, such as aliphatic, cycloaliphatic, aromatic and mixed tertiary amines, aliphatic heterocyclic amines such as N-methylpiperidine or N, N'-dimethylpiperidine as well as aromatic heterocyclic amines such as pyridine and pyrimidine. Other nitrogen compounds such as imidazole are indicated as being suitable. However, under the reaction conditions described tertiary amines as shown by van Landeghem do not catalyze urea decomposition.

Rosenthal et al U.S. Pat. No. 3,936,484 discloses the thermal decomposition of di- and tri-substituted ureas to isocyanates at temperatures above 230° C. in a solvent with short residence times and isocyanate yields of from 60 to 80%.

The Hearsey U.S. Pat. No. 3,898,259 describes the introduction of gaseous hydrogen chloride into the liquid phase urea decomposition reaction to give reduced reaction times with isocyanate yields of from 80–90%. An excess of gaseous HCl is employed at temperatures of from 100° to 200° C. and a by-product carbamoyl chloride intermediate formed.

A. Hentschel et al U.S. Pat. No. 4,223,145, Sept. 16, 1980 discloses the formation of an HCl adduct of a tri-substituted urea using at most, a 10% excess of HCl. This adduct is then decomposed in a closed system at from 80°–180° C.

Applicants have found that organic sulfonic acids are excellent promoters for the thermal decomposition of tri-substituted ureas to the corresponding isocyanates such as tolylene diisocyanates at relatively mild reaction temperatures and short residence times in an organic solvent. The reaction gives the corresponding isocyanate in almost quantitative yield.

SUMMARY OF THE INVENTION

This invention relates to a novel improved process for the preparation of aromatic mono- and polyisocyanates from aromatic bis dialkyl ureas which comprises thermally treating the aromatic bis dialkyl urea which has been dissolved in or slurried with an inert organic solvent in the presence of an organic sulfonic acid to produce the corresponding aromatic isocyanate. The aromatic isocyanates produced by the instant invention are of significant industrial importance and are particularly useful as intermediates in producing products for agricultural application and in the preparation of polyurethanes.

It is an object of the present invention, therefore, to provide an improved process for the production of aromatic mono- and polyisocyanates from trisubstituted ureas in high yield and high conversion of the ureas.

It is another object of this invention to provide an improved reaction (thermal decomposition) system for the conversion of aromatic bis (dialkyl) ureas to the corresponding aromatic isocyanates.

These and the other objects and advantages of this invention will become apparent from the description of the invention which follows, and from the claims.

DETAILED DESCRIPTION OF THE INVENTION

In accordance with the present invention aromatic mono-or polyisocyanates having the general formula

$Ar(NCO)_n$ wherein Ar is a mono-, di- or polyvalent aromatic radical which may be substituted with a halogen group, ether group, nitro group or an alkyl group having from 1 to 10 carbon atoms and n is a integer of from 1 to 3 are produced by heating at temperatures of from about 50° C. to 220° C. preferably from about 90° C. to 150° C. an aromatic bis dialkyl urea having the general formula Ar(NHCONR'R")$_n$ wherein Ar is as described above and R' and R", which may be the same or different, are alkyl groups having from 1 to 10 carbon atoms and n is an integer of from 1 to 3 dissolved in or slurried in an organic solvent or mixture of solvents, which are stable and substantially chemically inert to the components of the reaction system, in the presence of an organic sulfonic acid promoter such as alkane sulfonic, halogenated alkanesulfonic and aromatic sulfonic acids or acidic sulfonated aromatic ion exchange resins or perfluoroalkane sulfonic acid resins to convert the urea groups to isocyanate groups and the desired aromatic isocyanate product separated from the co-product dialkylamine sulfonate salt and recovered.

Referring to the general formulae set forth hereinabove Ar is preferably an aryl radical such as the mono-, di-, and trivalent radicals of benzene, toluene, naphthalene diphenyl, terphenyl and the like. The aryl radicals may carry from 1 to 3 dialkyl urea substituents and may have hydrogen atoms at the other ring positions or they may be substituted by one or more groups such as an alkyl group having from 1 to 10 carbon atoms, a halogen radical, a nitro group, an ether group, or other groups which are non reactive with the isocyanates produced and other components of the reaction system The R' and R" of the aromatic dialkyl urea formula set forth hereinabove may be substituted or unsubstituted mono-, di-, or trivalent radicals selected from saturated or monoolefinic unsaturated straight or branched chain aliphatic or cycloaliphatic radicals optionally containing alkoxyalkyl radicals with one or more ether linkages, aryl radicals, or aralkyl radicals. These radicals may be substituted with groups which are non-reactive with the isocyanates produced by the process of the invention, such as, for example, nitro or halo groups. Also included are cycloaliphatic and substituted cycloaliphatic radicals containing from 5 to 7 carbon atoms such as cyclopentyl, cyclohexyl and cycloheptyl radicals. Representative aromatic dialkyl urea compounds which may be employed in the process of the present invention include, for example, N-phenyl-N', N'-dimethylurea, N-phenyl-N', N'-diethylurea, N-phenyl-N'-methyl-N'-ethylurea, N-phenyl-N', N'-dicyclohexylurea, 2,4-tolylene-(bis diethylurea) 2, 6-tolylene- (bis dimethylurea), N-(2-chlorophenyl)-N', N'-bis (dicylohexyl) urea and the like. Aromatic dialkyl ureas and processes for their preparation have been described in the literature. Bis (dialkylureas) of toluene and other ureas may be prepared, for example, by reacting toluene-2,4-diisocyanate with diethylamine as described in Japanese Kokai No. 76/149,400. The urea compounds above described are merely representative of a large number of aromatic dialkyl ureas falling within the general formula above which can be converted to isocyanates in the solvent phase in the presence of an organic sulfonic acid as a promoter.

Representative aryl isocyanates which may be produced by the process of the present invention include, for example, phenyl isocyanate, 4-chlorophenyl and 2-fluorophenyl isocyanates 3,4-dichlorophenyl isocyanate, m-phenylene diisocyanate, 2,4-tolylene diisocyanate, 2,6-tolylene diisocyanate, 1, 5-naphthalene diisocyanate and the like compounds.

The organic sulfonic acids employed in the process of the present invention to promote the thermal decomposition of the aromatic mono- and polyisocyanates may be an alkane sulfonic acid or a halogenated alkane sulfonic acid having up to 10 carbon atoms in the alkyl group, or an aromatic sulfonic acid which may contain substituents on the aromatic ring such as halogens, alkyl radicals, aromatic radicals, nitro groups and the like. The organic sulfonic acid may be in the form of an acidic sulfonated aromatic ion exchange resin such as, for example, the sulfonated styrene/divinyl-benzene copolymer (sold, for example, commercially as "Amberlyst 15" by Rohm and Haas Co.) and having a bulk density of approximately 565 g./l., a hydrogen ion concentration of approximately 4.9 milliequivalents/g.dry, a surface area of from about 40 to 50M$^2$/g. and an average pore diameter of from about 200 to 600 Angstrom units, or an acidic perfluoroalkane sulfonic acid resin such as "Nafion" (sold for example, commercially by the DuPont Co.) and having an equivalent weight of between about 110 and 1500, a hydrogen ion concentration of between about 0.7–1.0 milliequivalents/g. dry and prepared, for example, by the polymerization of tetrafluoroethylene with a sulfonyl fluoride vinyl ether, followed by saponification with caustic to form the alkali metal salt and treatment with an acid to convert the salt to the sulfonic acid form. Mixtures of the sulfonic acid promoters may be employed but it is preferable to use a single acid promoter to simplify separation and recovery of the aromatic isocyanate produced. Representative organic sulfonic acid promoters suitable for use in the process of this invention include, for example, methane, ethane, butane, hexane sulfonic acids, and the like, trifluoromethane sulfonic acid, benzene sulfonic acid, 1,3-benzene disulfonic acid, p-toluene sulfonic acid, naphthalene sulfonic acid, 4-chloro-3-nitrobenzene sulfonic acid, 3-nitrobenzene sulfonic acid, and the like, as well as the sulfonated aromatic ion exchange resins which include the "Amberlyst 15" and "Nafion" described hereinabove and also include the "Dowex 50" (Dow Chemical), "AG50W" (Bio-Rad), and "Amberlite" (Rohm and Haas) resin materials. The ion exchange resins may be supplied commercially in the hydrogen ion form or the salt form such as the sodium or potassium salt. The salt can readily be converted to the active hydrogen ion form by, for example, treating with aqueous hydrochloric acid, washing with water to a constant pH in the range of 5.5 to 7 and then drying to remove residual water.

The organic sulfonic acid promoter is generally employed in the process of the instant invention at a molar ration of one to one based on the urea groups to sulfonic acid groups. No advantage is gained by using large excess amounts which may lead to by-product formation.

The process of the present invention can be suitably carried out by adding the aromatic bis dialkyl urea to a solvent or a mixture of solvents comprising the reaction medium. The urea may be soluble in the solvent or solvents or soluble at reaction temperatures or the urea may be in the form of a slurry. Reactions using a sulfonic acid ion exchange resin promoter may also be carried out in a fixed bed of resin by passing a solvent solution of the urea through the bed maintained at the desired reaction temperature. Suitable solvents which may be employed include, for example, the aromatic hydrocarbons such as benzene, toluene, xylene, trimethylbenzene, tetrahydronaphthalene, as well as the higher alkyl-substituted aromatic hydrocarbons; alkanes and substituted alkanes as well as cycloalkanes having from 5 to 20 carbon atoms such as, for example, n-hexane, n-heptane, octane, nonane, cyclohexane, dodecane, octadecane, 2-methylhexane, 2-ethylhexane, methylcyclohexane, and the like; halogenated or nitrated aromatic and aliphatic hydro carbons such as, for example, methylene chloride, carbon tetrachloride, 1,2-dichloroethane, tetrachloroethane, chlorobenzenes nitrobenzenes, dinitrotoluene and the like; aromatic or aliphatic ethers such as, for example diphenylether, dibutylether, propyleneglycol dimethyl ether, and the like; tertiary amines such as for example, pyridine, triethylamine, N-methylpyrrolidone and the like.

The process of the present invention may be carried out as a batch, semi-continuous or continuous process and the order of addition of the materials and reactants may be varied to suit the particular apparatus and sulfonic acid employed. For example, in a batch process all the dialkylurea, solvent and organic sulfonic acid may be charged together to the reaction vessel and then heated to the desired reaction temperature, or the urea and solvent may be added to the reactor as a solution or slurry and heated to the desired reaction temperature, and then the sulfonic acid promoter added alone or in additional solvent. The sulfonic acid promoter may also be added to the reactor, heated to the desired temperature and then the dialkyl urea added. The added materials can be maintained at any convenient temperature.

The reaction of the invention may be carried out in any suitable reactor which is equipped with a means for temperature control and agitation. Heating and/or cooling means may be employed interior or exterior of the reaction vessel to maintain temperature within the desired range.

As indicated hereinabove, the thermal decomposition of the aromatic bis dialkyl ureas is carried out at temperatures of from about 50° C. to about 220° C., preferably from about 90° C. to 150° C. Reaction time is dependent on decomposition temperature but will generally range between about 5 minutes and several hours. The reaction is generally carried out at atmospheric pressure, but depending on the boiling points of the solvents employed and the isocyanate product, it may be carried out at super-atmospheric or sub-atmospheric pressures. The isocyanate formed may be recovered by filtration, by distillation of either the solvent or the isocyanate, whichever is lower boiling, or by other known methods, and will depend on the solvent employed and the isocyanate produced.

The present invention is more fully illustrated by the following examples, which include particular features of the invention. However, the examples are not to be construed as limiting the invention in any way, it being understood that numerous variations are possible without department from the spirit and scope of the invention.

EXAMPLE 1

A mixture of 5.26 g, 16.4 mmoles, of 2,4-toluene bis (diethylurea) in 505 g toluene was added to a 1 liter, 3-neck, fluted, bottom flask equipped with a bottom take-off, mechanical stirrer, condenser and a thermocouple for measuring reaction temperature. The mixture was heated to gentle reflux at 110° C. and then 3.49 g, 36.3 mmoles, of methane sulfonic acid was added. The mixture was stirred for 15 min at 110° C. and then the mixture was allowed to settle at 60° C. The salt separated as a liquid bottom phase and was drawn off through the bottom take-off. The toluene phase was analyzed directly by infrared analysis for 2,4-toluene diisocyanate (TDI) by comparing the isocyanate band in the product with that in known standards of pure TDI in toluene. The yield of TDI was 98%. Another sample from the pot was treated with ethanol to convert the TDI to its ethyl carbamate derivative and this was analyzed by high pressure liquid chromatography (HPLC). This analysis, confirmed the infrared result, showed 100% conversion of the starting toluene bis (diethylurea) with 98% selectivity to TDI.

EXAMPLE 2

A jacketed blender reactor, as described by R. J. McCarter, Rev. Sci. Inst. 39,5 264, February, 1968, equipped with a condenser and a thermocouple for measuring reaction temperature was used. Steam was used to heat the jacket to the desired temperature. 6.19 g of 2,4-toluene bis (diethylurea) and 522 g o-xylene were charged to the reactor and heated to 130° C. using the high speed setting of the blender motor. Methane sulfonic acid, 4.44 g, was added in one portion and then samples were taken periodically from the o-xylene phase for infrared analysis. The yield of TDI was 94% after three minutes and 99% after 5 min mixing.

EXAMPLE 3

A mixture of 12.7 g 2,4-toluene bis (diethylurea) in 248 g o-xylene was charged to a 500 ml fluted flask equipped with a bottom take-off, a mechanical stirrer using a 1.5 inch "Teflon" crescent-shaped paddle, a condenser, and a thermocouple to monitor reaction temperature. The mixture was heated to 120° C. and then 8.75 g methane sulfonic acid was added in one portion. The mixture was stirred for 15 min at 120° C. and then the phases were allowed to settle at 50° C. The bottom salt phase was drawn off through the bottom take-off. Analysis of the xylene phase by HPLC and infrared analysis showed 100% conversion of the toluene bis (diethylurea) with a 98% yield of toluene diisocyanate. The xylene phase was then transferred to a round bottom flask equipped with a 12" Vigreux column and a distillation head for vacuum distillation. Octadecane, 65 g, was added to the flask and then the xylene was distilled overhead at 40 mm Hg. TDI was then distilled over 10 mm Hg. A heart cut of TDI containing 6.1 g TDI was obtained for an isolated yield of 88% for toluene diisocyanate.

EXAMPLES 4 to 11

A 250 ml round bottom flask equipped with a mechanical stirrer, condenser and thermocouple was used for the following runs. All reagents were charged initially, heated to the specified temperature for the time specified and then cooled to room temperature. The organic phase was analyzed for isocyanate by a combination of infrared and HPLC analysis. Reaction materials, conditions and analytical results are set forth in Table I.

TABLE I

EXAMPLES 4–11

| Ex. No. | Urea (g)* | Sulfonic Acid | Solvent (g) | Temp (°C.) | Time (Min) | Conversion of Urea (%) | Selectivity to NCO (%) |
|---|---|---|---|---|---|---|---|
| 4 | 2,4 TBDEU (3.2) | p-Toluene-SO3H (3.5) | Diphenylether (100) | 130 | 60 | 95 | 89 |
| 5 | 80%/20% mix 2,4-TBDMU/ 2,6-TBDMU (5.2) | CH3SO3H (3.9) | Octadecane (100) | 150 | 30 | 98 | 87 |
| 6 | 2,4-TBDMU (5.2) | CF3SO3H (6.0) | Toluene (100) | 90 | 10 | 99 | 97 |
| 7 | 80%/20% mix 2,4-TBDBU/ 2,6-TBDBU (4.3) | Benzene-SO3H (3.8) | Chlorobenzene (100) | 130 | 60 | 95 | 90 |
| 8 | DMPU (3.3) | CH3SO3H (2.0) | 1,2-Dichloro-ethane (100) | 80 | 120 | 90 | 97 |
| 9 | DEPU (9.6) | CH3SO3H (5.5) | Toluene (100) | 110 | 30 | 100 | 98 |
| 10 | 2,4-TBDMU (26.5) | CH3SO3H (18) | Mixed Xylenes | 140 | 15 | 99 | 98 |
| 11 | DEPU (3.8) | C2H5SO3H (2.4) | Toluene (100) | 110 | 45 | 98 | 95 |

*DMPU = 1-phenyl-3, 3-dimethylurea
DEPU = 1-phenyl-3, 3-diethylurea
2,4-TBDEU = 2,4-tolylenebis (diethylurea)
2,4-TBDMU = 2,4-tolylenebis (dimethylurea)
2,4-TBDBU = 2,4-tolylenebis (dibutylurea)
2,6-TBDEU = 2,6-tolylenebis (diethylurea)

EXAMPLE 12

A 250 g sample of "Dowex 50X2-400" (Dow Chemical Co.) ion exchange resin was washed with three 350 ml portions of hydrochloric acid to convert the resin to the hydrogen ion form. The resin was then washed with three 350 ml portions of distilled water and dried in a vacuum oven at 75° C. Ten grams of the dried resin was combined with 5.04 g of an 80%/20% mix of 2,4-toluene bis (diethylurea)/2,6-toluene bis (diethylurea) and 60 ml o-xylene in a round bottom flask. The mixture was heated at 144° C. for 4 hours under a nitrogen atmosphere. Throughout the reaction a slow nitrogen purge was maintained through the solution. At the end of the reaction time, the mixture was cooled to room temperature and the solid resin was removed by filtration. Analysis of the xylene solution by HPLC after addition of ethanol to convert the TDI to its ethyl carbamate derivative shows an 85% yield of toluene diisocyanate.

EXAMPLES 13 to 17

The following runs were made using the procedures of example 12. An 80%/20% mix of 2,4-toluene bis (diethylurea)/2,6-toluene bis (diethylurea) was used. Conditions and analytical results are set forth in Table 2 below.

TABLE 2

EXAMPLES 13 to 17

| Ex. No. | TBDEU (g) | Resin | Solvent (ml) | Temp (°C.) | Time (hr) | % Conversion BDEU | % Yield TDI |
|---|---|---|---|---|---|---|---|
| 13 | 5.04 | Amberlyst 15 (10) | Toluene | 110 | 4 | 50 | 40 |
| 14 | 5.01 | Dowex 50 × 2-200 (10) | Toluene | 110 | 4 | 45 | 38 |
| 15 | 5.03 | Dowex 50 × 2-200 (10) | 1,2-Dichloro-benzene | 180 | 4 | 100 | 80 |
| 16 | 5.05 | Dowex 50 × 8-400 (10) | o-xylene | 144 | 4 | 100 | 86 |
| 17 | 5.01 | Nafion NR50 (25) | o-xylene | 144 | 4 | 100 | 80 |

TBDEU = 80%/20% mix of 2,4-toluenebis (diethylurea) and 2,6-toluenebis (diethylurea)

We claim:

1. A process for the preparation of an aromatic mono- or poly- isocyanate having the formula $$Ar(NCO)_n$$

wherein Ar is a mono-, di- or poly-valent aromatic radical which may be substituted with a halogen, ether, or nitro group or an alkyl group having from 1 to 10 carbon atoms and n is an integer of from 1 to 3 which comprises heating at a temperature within the range of from about 50° C. to about 220° C. an aromatic bis dialkyl urea having the formula $$Ar(NHCONR'R'')_n$$

wherein Ar is as above described and R' and R" which may be the same or different, are an alkyl group having from 1 to 10 carbon atoms which may be substituted or unsubstituted mono-, di-, or tri-valent radicals selected from saturated or monoolefinic unsaturated straight or branched chain aliphatic or cycloaliphatic radicals and n is an integer of from 1 to 3, dissolved in or slurried in an organic solvent or mixture of solvents and in the presence of an organic sulfonic acid or sulfonated aromatic ion exchange resin as a promoter to convert the urea to the corresponding isocyanate, and thereafter separating and recovering the isocyanate.

2. A process according to claim 1 wherein the temperature is in the rang of from 90° C. to 150° C.

3. A process according to claim 1 wherein the aromatic bis (dialkyl) urea is selected from the group consisting of 1-phenyl-3, 3-diethyl urea, 1-phenyl-3, 3-dimethyl urea, 2,4-tolylene-bis (diethylurea), 2,6-tolylenebis (diethylurea), 2,4-tolylenebis (dimethylurea), and 2,6-tolylenebis (dibutylurea).

4. A process according to claim 3 wherein the aromatic bis (dialkyl) urea is a mixture of 2,4-tolyenebis (diethylurea) and 2,6-tolylenebis (diethylurea)

5. A process according to claim 1 wherein the organic solvent is selected from the group consisting of toluene, o-xylene, diphenyl ether, octadecane, 1,2-dichloroethane and chlorobenzene.

6. A process according to claim 5 wherein the organic solvent is o-xylene.

7. A process according to claim 5 wherein the organic solvent is 1,2-dichlorobenzene.

8. A process according to claim 1 wherein the organic sulfonic acid is selected from the group consisting of methane sulfonic acid, ethane solfonic acid, butane sulfonic acid, trifluoromethane sulfonic acid and benzene sulfonic acid.

9. A process according to claim 8 wherein the organic sulfonic acid is methanesulfonic acid.

10. A process according to claim 1 wherein the sulfonated aromatic ion exchange resin is selected from the group consisting of sulfonated styrene/divinylbenzene copolymer resins and acidic perfluoroalkane sulfonic acid resins.

11. A process for the preparation of 2,4-tolyene diisocyanate which comprises heating at a temperature in the range of from about 90° C. to about 150° C., 2,4-tolylenebis (diethylurea) in an organic solvent or mixture of solvents in the presence of an organic sulfonic acid and separating and recovering the 2,4-tolylene diisocyanate from the reaction mixture.

12. A process for the preparation of a mixture of 2,4-and 2,6- tolylene diisocyanate which comprises heating at a temperature in the range of from about 90° C. to about 150° C. a mixture of 2,4- and 2,6- tolylenebis (diethylurea) in an organic solvent or mixture of solvents in the presence of an organic sulfonic acid and separating and recovering the mixture of 2,4- and 2,6- tolylene diisocyanates from the reaction mixture.

13. A process according to claim 12 wherein a mixture of about 80% 2,4-tolylenebis (diethylurea) and 20% 2,4-tolylenebis (diethylurea) is employed.

14. A process for the preparation of 2,4-tolylene diisocyanate which comprises heating at a temperature in the range of from about 90° C. to about 150° C., 2,4-tolylene bis (diethylurea) in an organic solvent or mixture of solvents in the presence of a sulfonated aromatic ion exchange resin.

15. A process according to claim 14 wherein the sulfonated aromatic ion exchange resin is a sulfonated styrene/divinylbenzene copolymer resin.

16. A process according to claim 14 wherein the sulfonated aromatic ion exchange resin is a perfluoroalkane sulfonic acid resin.

* * * * *